United States Patent [19]

Strekopytov et al.

[11] Patent Number: 4,788,978

[45] Date of Patent: Dec. 6, 1988

[54] SURGICAL INSTRUMENT FOR APPLYING LINEAR STAPLE SUTURES AND INTERSECTING THE TISSUE THEREBETWEEN

[76] Inventors: Alexei A. Strekopytov, ulitsa Vsevoloda Vishnevskogo, 10 kv. 67; Boris A. Smirnov, ulitsa Borisa Galushkina, 17, kv. 26; Mikhail V. Danilov, ulitsa Bolshaya Cherkizovskaya, 10, korpus 2, kv. 145; Zaribbai Yangibaev, I Baltiisky pereulok, 3/25, kv. 225, all of Moscow, U.S.S.R.

[21] Appl. No.: 172,947

[22] Filed: Mar. 23, 1988

Related U.S. Application Data

[63] Continuation of Ser. No. 894,653, Aug. 8, 1986, abandoned, which is a continuation of Ser. No. 201,282, Oct. 27, 1980, abandoned.

[30] Foreign Application Priority Data

Nov. 23, 1979 [SU] U.S.S.R. .................. 2842286

[51] Int. Cl.⁴ ................. A61B 17/10; A61B 17/32
[52] U.S. Cl. ................. 128/334 R; 128/305; 227/DIG. 1
[58] Field of Search ........... 128/334 R, 334 C, 305, 128/346; 227/19, DIG. 1

[56] References Cited

U.S. PATENT DOCUMENTS

| 3,079,606 | 3/1963 | Bobrov et al. | 128/334 R |
| 3,683,925 | 8/1972 | Frankel | 128/346 X |
| 3,795,034 | 3/1974 | Strekopytov et al. | 128/334 R |

FOREIGN PATENT DOCUMENTS

| 2822803 | 12/1978 | Fed. Rep. of Germany | 128/334 R |
| 1379198 | 10/1964 | France | 128/334 R |
| 371926 | 5/1973 | U.S.S.R. | 128/334 R |

*Primary Examiner*—Michael H. Thaler
*Attorney, Agent, or Firm*—Burgess, Ryan & Wayne

[57] ABSTRACT

The surgical instrument for applying linear staple sutures comprises a supporting body with a supporting jaw having staple bending depressions. The staple body of the instrument is traversable inside the U-shaped supporting body from its own drive. The staple magazine is accommodated in the staple body and has a longitudinal recess with an open end to receive U-shaped staples adapted to be expelled from said magazine slots by means of an ejector. Part of the supporting jaw which carries the staple bending depressions is made detachable and has a groove. The supporting body has an opening arranged symmetrically to the longitudinal recess with an open end, both said opening and said longitudinal recess establishing in combination the gap for passing the knife blade traversable along the groove to sever the tissue between the sutures applied.

4 Claims, 1 Drawing Sheet

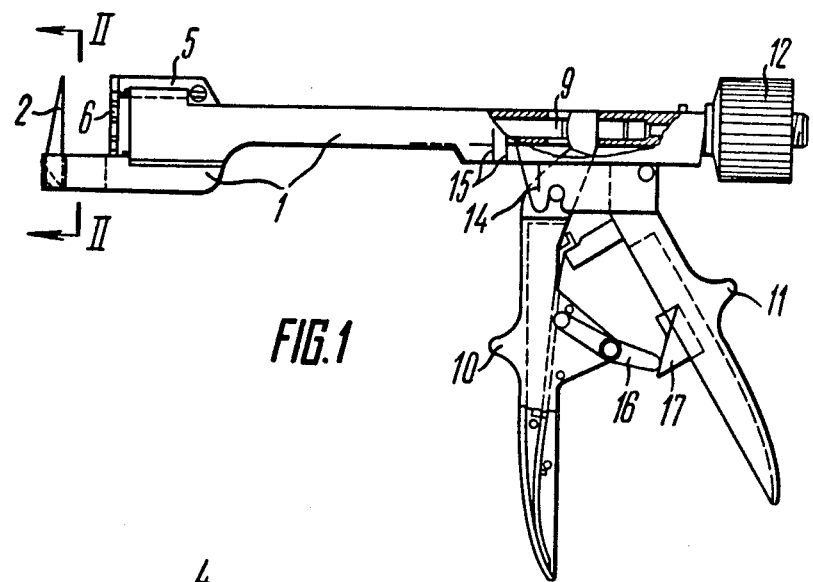
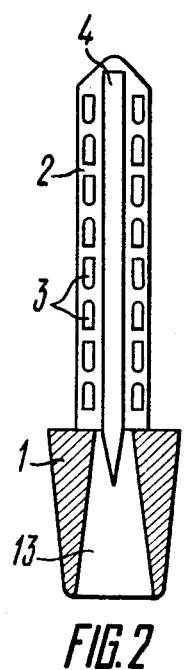
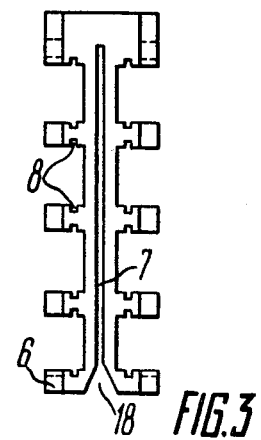
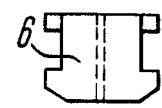
FIG.1
FIG.2
FIG.3
FIG.4

SURGICAL INSTRUMENT FOR APPLYING LINEAR STAPLE SUTURES AND INTERSECTING THE TISSUE THEREBETWEEN

This application is a continuation of application Ser. No. 894,653 filed Aug. 8, 1986 now abandoned, which is a continuation of application Ser. No. 201,282 filed Oct. 27, 1980 now abandoned.

FIELD OF THE INVENTION

The present invention relates to surgical instruments and is concerned more particularly with instruments for applying linear staple sutures and intersecting the tissue therebetween.

The invention is applicable in medical practice for stitching up various organs, particularly for applying linear staple sutures to the anterior wall of a stenosed exit portion of the common bile duct so as to stitch it with the adjacent wall of the duodenum and intersecting the tissue between the sutures applied, as well as for applying staple sutures to tissues situated in deep or narrow cavities.

BACKGROUND OF THE INVENTION

Restoration of the patency of a stenosed terminal portion of the common bile duct by way of direct incision thereof through the anterior duodenal wall is known to have found still wider application as such an operation resumes natural bile discharge, establishes decomposition of both the bile system and the pancreatic ducts, and provides for better postoperative results.

Up till now this operation has been performed manually both in this country and abroad. However, manually carrying out this operation involves troubles in fixing and apposing the lips of the incised bile duct and duodenum, which may be accompanied by bleeding from the wound lips. Furthermore the line of sutures frequently proves to be uneven, inflammation is sustained for a prolonged period of time within the suture application zone, and biliary calculi tend to settle upon the suturing threads.

A great many surgical instruments for applying linear staple sutures and intersecting the tissue therebetween are known (cf., e.g., USSR Inventor's Certificate No. 125,867 Int. Cl. A61B 17/11 published in 1960), which are adapted to carry out surgical operations on the gastrointestinal tract.

Such surgical instruments mechanize the labour-consuming and lengthy process of manual application of surgical sutures. Of paramount importance is the fact that apart from considerably reducing the suture application time these instruments provide for a required degree of asepsis, tightness and hemostasis of the sutures applied, and correct arrangement of separate stitches, as well as reduce the amount of traumatism of the walls of the organs being sutured and of the adjacent tissues which favourably affects the course of the postoperative period. Moreover, the quality of operations is to a lesser extent dependent upon the surgeon's skill as compared to manual suturing.

However, the heretofore known surgical instruments for applying linear staple sutures and intersecting the tissue therebetween are generally not used in operations for restoring the patency of a stenosed terminal portion of the common bile duct, this being due to their constructional features, viz., the fact that the supporting jaw is arranged on the same axis with the mechanical actuator, whereby the entire instrument has to be introduced into the operative wound along with the surgeon's hand.

Another heretofore known surgical instrument for applying linear staple sutures and intersecting the tissue therebetween, adapted for stitching up blood vessels with two double-stitch sutures and simultaneously intersecting these vessels (cf. USSR Inventor's Certificate No. 371,926 Int. Cl. A61B 17/11, published in 1973) is adopted herein as the prototype.

The known instrument in question comprises an oblong u-shaped supporting body with a supporting jaw, which has depressions for bending of the staple and a die, a staple body having a carriage and a tail-piece and adapted to travel inside the u-shaped supporting body from its own drive, a staple magazine situated in the carriage of the supporting body and provided with a closed slot for the knife blade to pass and a number of slots for accommodating u-shaped staples expelled from these slots by means of an ejector.

This instrument is applicable whenever it becomes necessary to sever a vessel and apply a hermetically tight suture to both of its stumps, which is the case in, for example, treatment of pulmonary vessels in adult patients and major pulmonary vessels in children, as well as in abdominal surgery and surgery of the limbs.

However, the instrument features a heavy-section supporting jaw, which impedes insertion of the working member of the instrument into small diameter tubular organs or passing the same through narrow passages, specifically into the exit portion of the common bile duct, this being due to the fact that the supporting jaw carries an intermediate T-shaped bar, a die held thereto and a plastic backing pad. Besides, the supporting jaw tends to be weakened due to the presence of a slot adapted to accommodate part of the T-shaped bar and a number of holes.

The ejector of the known instrument is a rod with a head, whereon staple expelling prongs are secured and a detachable knife is situated therebetween.

Such a constructional arrangement of the staple ejector renders the known instrument inconvenient in handling since the knife must be sufficiently sharp for every operation, whereas final dressing of the knife is a complicated task requiring specialists to be carried out.

Provision of a plastic backing pad in the die slot brings about one more inconvenience in operation of the known instrument as the backing pad must be replaced for a succeeding operation.

BRIEF DESCRIPTION OF THE INVENTION

The present invention is aimed at the provision of a surgical instrument for applying linear staple sutures and intersecting the tissue therebetween, wherein the supporting jaw has a minimized section, and the supporting body and staple magazine are made as to provide a minimum amount of marginal tissues caught to the line of suture, enable the knife blade to be introduced and improve the conditions for severing the tissue between the sutures applied.

It is a primary and essential object of the present invention to facilitate introduction of the working member of the instrument into small openings or its passing through narrow passages, in particular into a stenosed exit portion of the common bile duct.

It is another object of the present invention to minimize the amount of marginal tissues caught to the line of suture, enable the knife blade to be introduced and improve the conditions for severing the tissue between the sutures applied.

It is one more object of the present invention to cut down the operating time and improve the outcome of the operation.

In some of its other aspects the present invention provides enhanced convenience in the handling of the instrument and simplifies its construction.

According to the aforesaid and other objects the present invention consists in that in a surgical instrument for applying linear staple sutures and intersecting the tissue therebetween, comprising an oblong u-shaped supporting body provided with a supporting jaw, which has staple bending depressions formed therein, a staple body traversable inside the u-shaped supporting body from its own drive, a staple magazine accommodated in the staple body and having a longitudinal recess with an open end through which a knife blade can pass and slots adapted to accommodate u-shaped staples expelled from the magazine slots by means of an ejector, according to the present invention, the staple bending depressions are provided in that portion of the supporting jaw, which is made detachable with respect to the supporting body and has a groove, while the supporting body has an opening arranged symmetrically to the longitudinal recess with an open end so that the opening and the longitudinal recess define a gap for the knife blade traversing along the groove to pass through said gap and intersect the tissue between the sutures applied.

Detachable construction of the supporting jaw portion, wherein staple bending depressions and a groove are provided enables the jaw section to be reduced considerably due its being made as a solid single bar, thus facilitating introduction of the instrument working member into small-diameter tubular organs or passing it through narrow passages, specifically into a stenosed exit portion of the common bile duct.

Provision of a gap for the knife blade traversable along the groove to pass therethrough makes possible a quality severing of the tissue between the sutures applied.

BRIEF DESCRIPTION OF THE DRAWINGS

In what follows the present invention is illustrated in a specific embodiment thereof given with reference to the accompanying drawings, wherein:

FIG. 1 is a general schematic view of the surgical instrument for applying linear staple sutures and intersecting the tissue therebetween, according to the present invention;

FIG. 2 is a section taken along the line II—II in FIG. 1;

FIG. 3 is a plan view of the staple magazine of the herein-disclosed instrument, featuring a longitudinal recess for the knife blade to pass and a number of slots for the u-shaped staples to accommodate, according to the present invention; and FIG. 4 is an end elevational view of FIG. 3.

DETAILED DESCRIPTION OF THE INVENTION

The instrument comprises an oblong u-shaped supporting body 1 provided with a detachable supporting jaw 2, which has a number of staple bending depressions 3 and a blind or non-through groove 4. The instrument also incorporates a staple body 5 traversable inside the u-shaped supporting body 1 from its own drive, a staple magazine 6 accommodated in the staple body 5 and having a longitudinal recess 7 with an open end for the knife blade to pass and slots 8, wherein u-shaped staples are housed, which are expelled from said slots 8 of the magazine 6 by an ejector 9 through an actuator including handles 10 and 11. The drive for the staple body is constituted by a screw pair and associated nut 12.

The detachable supporting jaw 2 of the supporting body 1 provided with the staple bending depressions 3 and the groove 4 is made as a solid unitary bar, whereby the section of the supporting jaw 2 is considerably reduced.

The supporting body 1 has an opening 13, which defines, together with the longitudinal recess 7 of the magazine 6, a gap for the knife blade traversable along the groove 4 to pass through the gap and sever the tissue between the applied sutures, said longitudinal recess 7 having an open end and being arranged symmetrically to said opening 13.

A throw-away safety-razor blade is used for severing the tissue between linear rows of staple sutures applied, which can easily be cut to pieces by conventional scissors. One piece of a safety-razor blade is secured in a holder (not shown), a stop being provided at the end of the holder arm to fix the blade against turning. The working end of the blade must be cut an angle less than 90°. This dispenses with a necessity to dress the knife blade to a required sharpness prior to each operation.

The degree of compression of tissues and their thickness are found either by a meter with a preset force, whereupon the thus-measured dimension is set against the suturing gap scale, or by surgeon's personal handfeel. In both case an alignment mark 14 provided on the staple body 5 must be situated between alignment marks 15 provided on the supporting body 1 to indicate the zone of correct staple bending.

The handles 10 and 11 have respectively a preventer piece 16 to ensure against premature suturing, and a stop 17. In addition, the magazine 6 is equipped with guides 18 to facilitate introducing of the knife blade.

The instrument operates as follows.

The anterior wall of the major duodenal papilla (the stenosed end of the common bile duct) is raised a little by two thread-type stay sutures. Then the supporting jaw 2 is introduced into the papilla for a length of 0.5 to 2.0 cm depending upon the stenosed length of the duct. If the exit aperture of the papilla is badly stenosed, its wall may be first severed by vascular scissors for a length of 2 to 5 mm (the segment that usually need not be sutured). Next the supporting jaw 2 is introduced into the stenosed aperture of the papilla, whereupon the nut 12 is rotated clockwise to shift the staple body 5 along with every component situated thereon with respect to the supporting jaw 2, thereby reducing the gap between the contact surfaces of the magazine 6 and the contact surface of the supporting jaw 2. In every case the alignment mark 14 must be situated between the alignment marks 15 which define the zone of correct staple bending. Then the preventer piece 16 is disengaged from the stop 17 and the handles 10 and 11 are brought all the way together, thus causing the ejector 9 to move and expel the staples out of the slots 8 in the magazine 6. The staple leg pierce the anterior wall of the papilla along with the adjacent duodenal wall and get into the depressions 3 of the supporting jaw 2 to be bent into the B-shape, thus establishing two-row linear suture.

A piece of a safety-razor blade secured in the holder, is passed via the opening 13, the guides 18 and the longitudinal recess 7 with an open end until it meets the web of the magazine 6. Then the blade end is pressed towards the groove 4 and the blade is passed towards the opening 13, thus severing the tissue of the papilla nd duodenum between the linear staple sutures applied. Next one must turn the nut 12 counterclockwise to withdraw the magazine 6 from the supporting jaw 2 and bring the instrument out of the operative wound.

This terminates the operation for eliminating differential stenosis of the papilla (the exit portion of the common bile duct).

As a result the operating time is cut down to 1 or 2 minutes as compared with 20 to 30 minutes in the case of a manual operation. The sutures thus applied feature perfect tightness, accurate adaptation of the tissues being sutured, even incision margins, reduced danger of damaging the pancreatic duct and lithogenesis at the edges of the line of sutures. Reaction to metallic suture material (staples) is many times as low as compared to silk. Thus, conditions are provided for considerable amelioration of both short-and long-term results of restoration of the patency of a stenosed exit portion of the common bile duct.

What is claimed is:

1. A surgical instrument for applying linear staple sutures comprising:

an elongated supporting body extending in a first direction;

a supporting jaw formed as a one-piece monolithic structure, said supporting jaw being mounted at one of its ends to said supporting body so as to extend substantially transversely with respect thereto, said supporting jaw having a plurality of staple bending depressions provided therein formed in a pair of substantially linear rows, and wherein a blind or non-through groove is formed in said supporting jaw extending parallel to and between said rows of staple bending depressions;

said supporting body having an elongated through opening arranged therein adjacent said supporting jaw;

a staple body accommodated in said supporting body and adapted to traverse the same;

means for moving said staple body toward and away from said supporting jaw;

a staple magazine accommodated on said staple body and having a plurality of staple receiving slots provided therein formed in a pair of substantially linear rows corresponding to said staple bending depressions, said magazine having a longitudinal recess formed therethrough extending between said rows of staple receiving slots, said longitudinal recess having an end opening externally of said staple magazine into open communication with said elongated through opening and being substantially symmetrical therewith, said longitudinal recess extending the entire width of said staple magazine in said first direction to enable an external knife blade to be inserted through said through opening and into said longitudinal recess, regardless of the distance between said staple magazine and said supporting jaw, after a suturing operation, to permit traverse of said knife blade along said groove formed in said supporting jaw between said rows of staple bending depressions to sever the tissue between the two rows of applied sutures; and means for ejecting said staples from said staple magazine.

2. A surgical instrument according to claim 1;

wherein said means for moving includes an elongated rod extending along the length of said elongated supporting body, said rod being connected at one end to said staple body and having screw threads at an opposite end thereof, and a nut screw-threadedly received on the screw-threaded end of said rod and mounted to said body for moving said rod and said staple body toward and away from said supporting jaw upon rotation of said nut.

3. A surgical instrument according to claim 1;

further including actuating means for actuating said means for ejecting so that said staples are ejected from said slots of said staple magazine, said actuating means including first handle means fixedly secured to said body and second handle means pivotally secured to said body for actuating said means for ejecting upon pivotal movement of said second handle means toward said first handle means.

4. A surgical instrument according to claim 3;

further including lock means for preventing pivotal movement of said second handle means toward said first handle means, as said lock means including a pivotal projection on one of said first and second handle means, as said pivotal projection being pivotal between a first position which permits movement of said second handle means toward said first handle means and a second position which prevents movement of said second handle means toward said first handle means.

* * * * *